(12) United States Patent
Huang et al.

(10) Patent No.: US 8,939,906 B2
(45) Date of Patent: Jan. 27, 2015

(54) WIRELESS INTRAOCULAR PRESSURE MONITORING DEVICE, AND DETECTING MODULE THEREOF

(71) Applicant: National Chiao Tung University, Hsinchu (TW)

(72) Inventors: Tzuen-Hsi Huang, Hsinchu (TW); Ying-Chun Lin, Taichung (TW); Wei-Shang Su, Taipei (TW); Huey-Wen Cheng, Taichung (TW); Hong-Yi Huang, Taipei (TW); Ching-Hsing Luo, Tainan (TW); Jin-Chern Chiou, Hsinchu (TW)

(73) Assignee: National Chiao Tung University, Hsinchu (TW)

( * ) Notice: Subject to any disclaimer, the term of this patent is extended or adjusted under 35 U.S.C. 154(b) by 191 days.

(21) Appl. No.: 13/845,843

(22) Filed: Mar. 18, 2013

(65) Prior Publication Data
US 2014/0275936 A1 Sep. 18, 2014

(51) Int. Cl.
*A61B 5/00* (2006.01)
(52) U.S. Cl.
USPC .......................................................... 600/398
(58) Field of Classification Search
USPC ................................................. 600/398–400
See application file for complete search history.

(56) References Cited

U.S. PATENT DOCUMENTS

| | | | | |
|---|---|---|---|---|
| 6,443,893 | B1 * | 9/2002 | Schnakenberg et al. | 600/398 |
| 6,749,568 | B2 * | 6/2004 | Fleischman et al. | 600/399 |
| 6,939,299 | B1 * | 9/2005 | Petersen et al. | 600/398 |
| 7,137,952 | B2 * | 11/2006 | Leonardi et al. | 600/398 |
| 7,499,377 | B2 * | 3/2009 | Jaworski et al. | 367/157 |
| 8,475,374 | B2 * | 7/2013 | Irazoqui et al. | 600/398 |
| RE45,013 | E * | 7/2014 | Miwa | 351/211 |
| 8,857,981 | B2 * | 10/2014 | Pletcher et al. | 351/158 |

* cited by examiner

*Primary Examiner* — Max Hindenburg
(74) *Attorney, Agent, or Firm* — Stroock & Stroock & Lavan LLP

(57) ABSTRACT

A wireless intraocular pressure monitoring device includes reflecting and detecting modules. The reflecting module includes a soft contact lens having a curvature corresponding to that of a cornea while worn. A metal layer is embedded in and deformable with the soft contact lens. The detecting module includes two waveguides, an oscillator, and a converting unit. The oscillator is operable to generate oscillation signals having a frequency dependent on an equivalent impedance of the waveguides such that the equivalent impedance corresponds to intraocular pressure. The converting unit is operable for receiving and converting the oscillation signals into an output signal corresponding to the intraocular pressure.

6 Claims, 3 Drawing Sheets

WIRELESS INTRAOCULAR PRESSURE MONITORING DEVICE, AND DETECTING MODULE THEREOF

BACKGROUND OF THE INVENTION

1. Field of the Invention

This invention relates to an intraocular pressure monitoring device, more particularly to a wireless intraocular pressure monitoring device.

2. Description of the Related Art

Glaucoma, one of the eye diseases that lead to vision loss, may be categorized into chronic simple glaucoma and acute congestive glaucoma. Chronic simple glaucoma, also known as open-angle glaucoma, accounts for approximately 90% of the cases in the U.S., is characterized by a gradual rise in intraocular pressure, and does not cause pain. On the other hand, acute congestive glaucoma, also known as narrow-angle glaucoma, is less common and is characterized by a sudden rise in intraocular pressure generally attributed to blockage of the drainage route of the aqueous humor. Symptoms associated with this type of glaucoma may be alleviated by using certain types of eye drops to improve drainage of the aqueous humor and/or using certain drugs (e.g., diuretics) to suppress secretion of the aqueous humor.

According to the statistics of the World Health Organization (WHO), there are approximately 67 million cases of glaucoma worldwide, among which 6.4 million cases progressed to complete vision loss. Moreover, the elderly accounts for 75% of the 6.4 million cases. The statistics further show that, among the population of age 40 or above (currently 3 million people), 0.12 million people suffered vision loss due to glaucoma.

Currently, glaucoma cannot be cured, and symptoms and development of which can only be suppressed through the use of drugs and/or through surgical operations, which aim to reduce the intraocular pressure so as to prevent damage to the optic nerves. Relevant researches further indicate that the main cause of glaucoma has been the variation in intraocular pressure, and that people who are diagnosed with diabetes, who have high blood pressure or myopia, and who have family members suffering from glaucoma are at high risk of developing glaucoma.

Therefore, timely control of intraocular pressure is the most important part of controlling the development of glaucoma. That is to say, regular monitoring of intraocular pressure is important, especially in finding out the cause of a rise in the intraocular pressure of a patient. However, since access to relevant medical equipments is generally limited due to their prices and sizes, people with glaucoma are generally unaware of their own biological statuses.

Referring to FIG. 1, U.S. Pat. No. 7,137,952 discloses a conventional non-invasive wireless intraocular pressure monitoring device including a sensor unit 1, an interrogation unit 14, a wireless receiver unit 15, and a computer device 16.

The sensor unit 1 includes a soft contact lens 101 made of silicone, an active resistive strain gauge 10, a passive resistive strain gauge 11, a low-power transponder 12, and an antenna 13. The active and passive resistive strain gauges 10, 11 are arranged to form a Wheatstone bridge structure and are embedded in the soft contact lens 101. The active resistive strain gauge 10 has a resistance that varies based on a variation in curvature of the soft contact lens 101, which may be caused by a change in curvature of the cornea attributed to a change in the intraocular pressure. The passive resistive strain gauge 11, on the other hand, is operable to provide a temperature-based compensation for correcting errors associated with the variation in the resistance. Next, the resistance may be converted into a sensor voltage corresponding to the intraocular pressure.

The low-power transponder 12 is connected electrically to the Wheatstone bridge structure, and is operable to perform a first modulation process upon the sensor voltage so as to generate a first carrier-frequency signal for wireless transmission to the interrogation unit 14 via the antenna 13.

The interrogation unit 14 is operable to wirelessly power the low-power transponder 12, to wirelessly receive the first carrier-frequency signal from the low-power transponder 12, and to perform a first demodulation process upon the first carrier-frequency signal received thereby so as to obtain a demodulated voltage corresponding to the sensor voltage. The interrogation unit 14 is further operable to perform an analog-to-digital conversion process upon the demodulated voltage so as to obtain a digital signal corresponding to the sensor voltage, and to subsequently perform a second modulation process upon the digital signal so as to obtain a second carrier-frequency signal for wireless transmission to the wireless receiver unit via an antenna.

The wireless receiver unit 15 is operable to wirelessly receive the second carrier-frequency signal from the interrogation unit 14, and to perform a second demodulation process upon the second carrier-frequency signal received thereby so as to obtain demodulated data corresponding to the sensor voltage.

The computer device 16 is connected electrically to the wireless receiver unit 15 for receiving the demodulated data therefrom, and is operable to output an intraocular pressure value based on the demodulated data with reference to a conversion table that defines a plurality of relationships between a plurality of data values and a plurality of corresponding intraocular pressure values, respectively.

However, the sensor unit 1 of the conventional intraocular pressure monitoring device includes many components such that a relatively complicated and expansive manufacturing process is needed for producing the sensor unit 1 with a complex structure. Therefore, there is a need in the art to provide an intraocular pressure monitoring device that requires a relatively simple manufacturing process and that incurs a relatively low production cost.

SUMMARY OF THE INVENTION

Therefore, the object of the present invention is to provide a wireless intraocular monitoring device that may overcome the aforesaid drawback of the prior art.

According to this invention, a wireless intraocular monitoring device comprises:

a reflecting module including
    a soft contact lens for wearing on a cornea such that a curvature of the soft contact lens corresponds substantially to that of the cornea, and
    a metal layer embedded in the soft contact lens and deformable together with the soft contact lens when the soft contact lens is worn on the cornea; and
a detecting module including
first and second waveguides,
an oscillator coupled to the first and second waveguides and operable to generate first and second oscillation signals that are substantially 180° out-of-phase, that are fed to the first and second waveguides respectively, and that have a frequency dependent on an equivalent impedance of the first and second waveguides, one of the first and second waveguides wirelessly transmitting an electromagnetic wave for reflection by the metal layer of the reflecting module, the other one of the first and second waveguides wirelessly receiving the electromagnetic wave reflected by the metal layer, the equivalent impedance of the first and second waveguides varying according to the electromagnetic wave reflected by and received from the reflecting module such that the equivalent impedance of the first and second waveguides further corresponds to intraocular pressure when the soft contact lens is worn on the cornea, and a converting unit coupled to the oscillator and operable for receiving at least one of the first and second oscillation signals and for converting the frequency of the at least one of the first and second oscillation signals into an output signal corresponding to the intraocular pressure.

BRIEF DESCRIPTION OF THE DRAWING

Other features and advantages of the present invention will become apparent in the following detailed description of the preferred embodiment of this invention, with reference to the accompanying drawings, in which.

DETAILED DESCRIPTION OF THE PREFERRED EMBODIMENT

Figure 1:
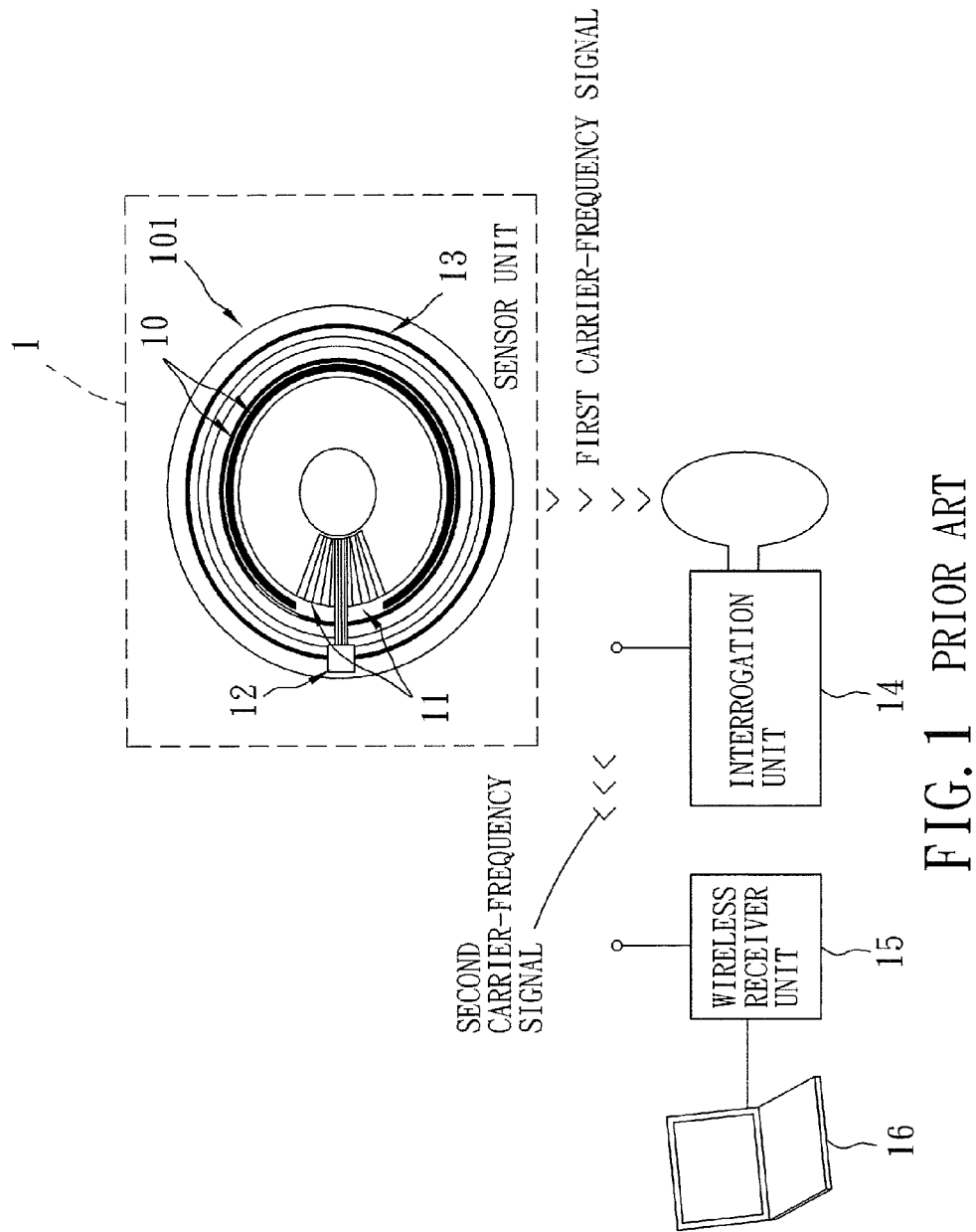
FIG. 1 is a block diagram of a conventional wireless intraocular pressure monitoring device.
Figure 2:
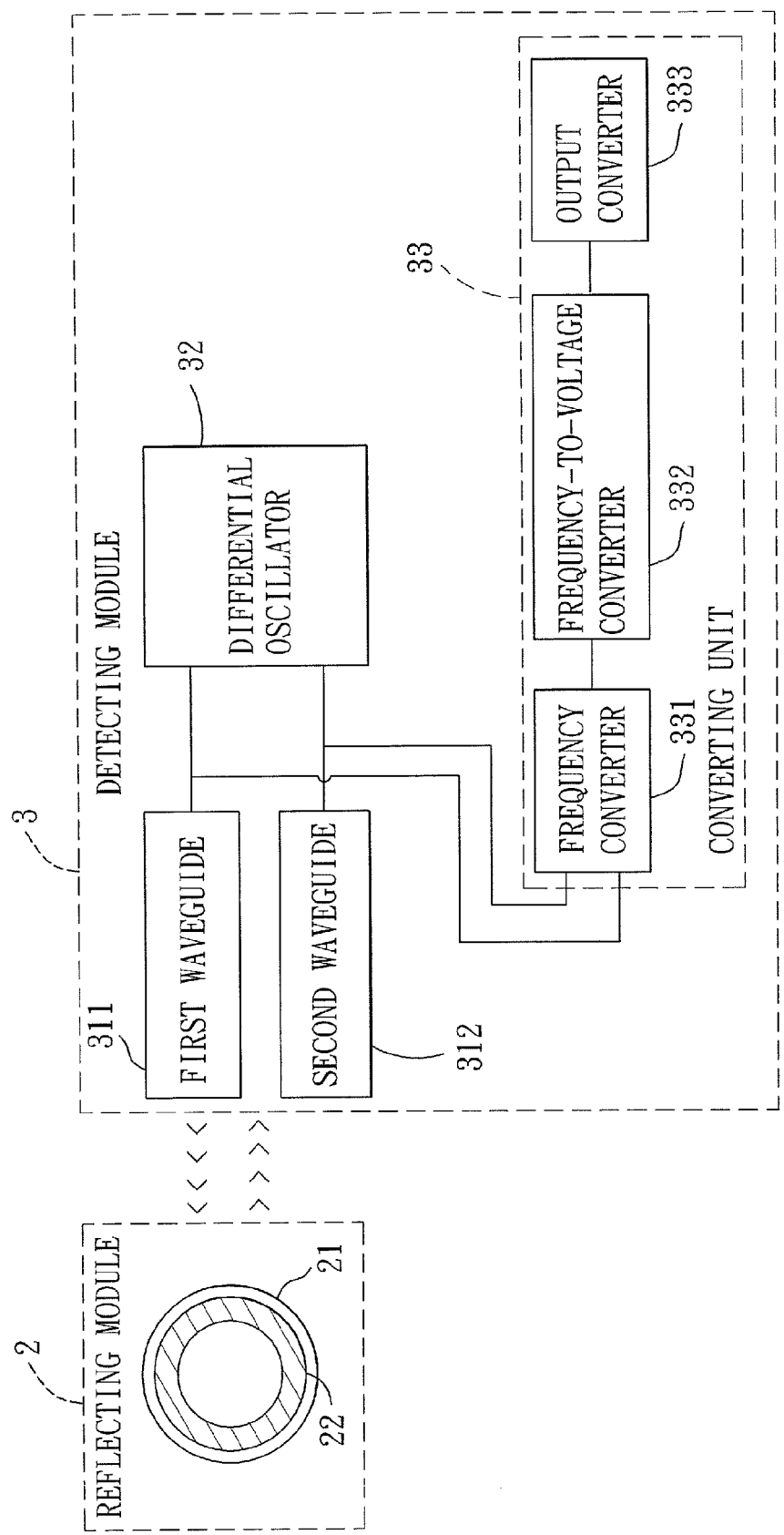
FIG. 2 is a block diagram of a wireless intraocular pressure monitoring device of a preferred embodiment according to the present invention.
Figure 3:
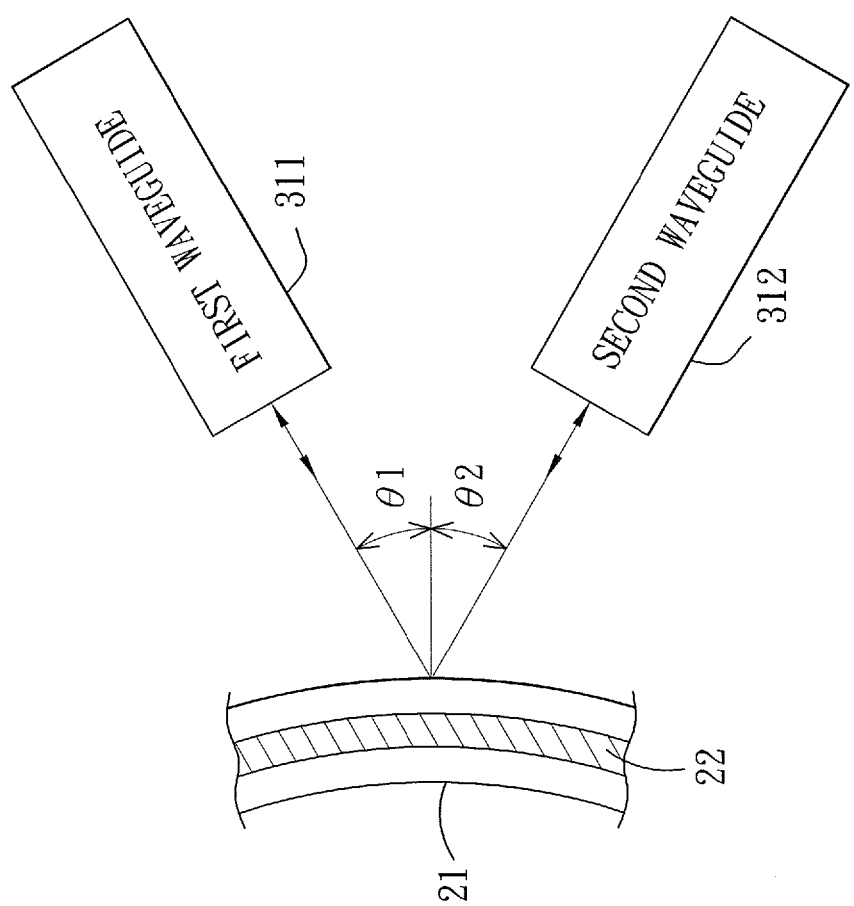
FIG. 3 is a schematic diagram illustrating an electromagnetic wave being transmitted to and reflected from a metal layer in the preferred embodiment according to the present invention.

Referring to FIGS. 2 and 3, a preferred embodiment of a wireless intraocular pressure monitoring device in accordance with the present invention includes a reflecting module 2 and a detecting module 3. The reflecting module 2 includes a soft contact lens 21 and a metal layer 22. The detecting module 3 includes a first waveguide 311, a second waveguide 312, a differential oscillator 32, and a converting unit 33.

The soft contact lens 21 is adapted for being worn on a cornea (not shown) of an eye (not shown), such that the curvature of the soft contact lens 21 corresponds substantially to that of the cornea. Preferably, the soft contact lens 21 is made of hydroxyethylmethacrylate (HEMA) for high oxygen permeability and comfortable long-duration wearing.

The metal layer 22 is embedded in the soft contact lens 21 and deformable together with the soft contact lens 21. Preferably, the metal layer 22 is made of gold or titanium. In this embodiment, the metal layer 22 is configured in an annular shape to prevent covering a pupil of the eye. Note that in other embodiments, the metal layer 22 may be configured in other shapes for different circumstances, for example, to cover the pupil in cases where eye vision is not a consideration.

The differential oscillator 32 of the detecting module 2 is coupled to the first and second waveguides 311 and 312, and is operable to generate first and second oscillation signals that are substantially 180° out-of-phase, that are fed to the first and second waveguides 311 and 312 respectively, and that have a frequency dependent on an equivalent impedance of the first and second waveguides 311 and 312 looked at output nodes of the differential oscillator 32. One of the first and second waveguides 311 and 312 wirelessly transmits an electromagnetic wave for reflection by the metal layer 22 of the reflecting module 2, and the other one of the first and second waveguides 311 and 312 wirelessly receives the electromagnetic wave reflected by the metal layer 22. The equivalent impedance of the first and second waveguides 311 and 312 varies according to the electromagnetic wave reflected by and received from the reflecting module 2. Variation of the intraocular pressure of the eye is a cause of to the curvature change of the cornea. Therefore, when the soft contact lens 21 is worn on the cornea, variation in curvature of the cornea leads to the curvature change of the soft contact lens 21, thereby resulting in deformation of the metal layer 22. Such deformation causes the changes of the incident/reflecting angles $\theta_1$ and $\theta_2$ of the electromagnetic wave on the metal layer 22, so as to change the equivalent wavelength of the electromagnetic wave received by one of the first and second waveguides 311 and 312. The equivalent impedance of the first and second waveguides 311 and 312 thus varies upon the change of the equivalent wavelength of the electromagnetic wave attributed to the intraocular pressure variation.

It should be noted that both the first and second waveguides 311 and 312, which behave like an aperture antenna in a radar system, transmit and receive the electromagnetic wave simultaneously. When the first waveguide 311 transmits the electromagnetic wave, the second waveguide 312 receives the electromagnetic wave reflected from the metal layer 22. On the other hand, when the second waveguide 312 transmits the electromagnetic wave, the first waveguide 311 receives the electromagnetic wave reflected from the metal layer 22. Accordingly, a signal path link exists between the first and second waveguides 311 and 312 by means of the wave reflection caused by the reflection module 2.

The converting unit 33 is coupled to the differential oscillator 32 and is operable for receiving at least one of the first and second oscillation signals (shown in FIG. 2), and for converting the frequency of the at least one of the first and second oscillation signals into an output signal which corresponds to the intraocular pressure.

In this embodiment, the converting unit 33 includes a frequency converter 331, a frequency-to-voltage converter 332, and an output converter 333. The frequency converter 331 is coupled to the differential oscillator 32 and is operable to reduce the frequency of the at least one of the first and second oscillation signals so as to generate a reduced-frequency signal. The frequency-to-voltage converter 332 is coupled to the frequency converter 331 and is operable to perform frequency-to-voltage conversion upon the reduced-frequency signal so as to obtain a converted voltage. The output converter 333 is coupled to the frequency-to-voltage converter 332 and is operable to convert the converted voltage into the output signal.

In this embodiment, the frequency-to-voltage converter 332 is implemented using a phase-locked loop (PLL). However, the scope of the present invention is not limited in this regard. It should be noted that, in other embodiments, the frequency-to-voltage converter 332 may be substituted with a frequency-to-current converter which is operable to perform a frequency-to-current conversion upon the reduced-frequency signal so as to obtain a converted current, and the output converter 333 correspondingly is operable to convert the converted current into the output signal.

In this embodiment, the output converter 333 is to perform an analog-to-digital conversion of the converted voltage so as to generate a digital signal, followed by performing a predetermined mathematical calculation (defining a relationship between the digital signal and the intraocular pressure) upon the digital signal to obtain the output signal. It should be noted that, in other embodiments, the output converter 333 may be operable to perform an analog-to-digital conversion so as to generate a digital signal. The output signal may be obtained with reference to a predetermined lookup table that defines the relationship between the digital signal and the intraocular pressure, responsive to the digital signal.

To sum up, the preferred embodiment described herein has the following advantages:

(1) The reflecting module 2, which includes only the soft contact lens 21 and the metal layer 22, is much easier to manufacture compared to the conventional intraocular pressure monitoring device described herein above.

(2) When the frequency of the first and second oscillation signals is higher than 20 GHz, size of the first and second waveguides 311 and 312 can be reduced, such that the detecting module 3 may be small enough to be configured on an article (such as eye glasses), a handheld article, or a testing platform, and the wireless intraocular pressure monitoring device in accordance with the present invention thus has a more extensive scope of applications.

While the present invention has been described in connection with what is considered the most practical and preferred embodiment, it is understood that this invention is not limited to the disclosed embodiment but is intended to cover various arrangements included within the spirit and scope of the broadest interpretation and equivalent arrangements.

What is claimed is:

1. A wireless intraocular pressure monitoring device comprising:
    a reflecting module including
        a soft contact lens for wearing on a cornea such that a curvature of said soft contact lens corresponds substantially to that of the cornea, and
        a metal layer embedded in said soft contact lens and deformable together with said soft contact lens when said soft contact lens is worn on the cornea; and
    a detecting module including
        first and second waveguides,
        an oscillator coupled to said first and second waveguides and operable to generate first and second oscillation signals that are substantially 180° out-of-phase, that are fed to said first and second waveguides respectively, and that have a frequency dependent on an equivalent impedance of said first and second waveguides, one of said first and second waveguides wirelessly transmitting an electromagnetic wave for reflection by said metal layer of said reflecting module, the other one of said first and second waveguides wirelessly receiving the electromagnetic wave reflected by said metal layer, the equivalent impedance of said first and second waveguides varying according to the electromagnetic wave reflected by and received from said reflecting module such that the equivalent impedance of said first and second waveguides further corresponds to intraocular pressure when said soft contact lens is worn on the cornea, and
        a converting unit coupled to said oscillator and operable for receiving at least one of the first and second oscillation signals and for converting the frequency of the at least one of the first and second oscillation signals into an output signal corresponding to the intraocular pressure.

2. The wireless intraocular pressure monitoring device as claimed in claim 1, wherein said oscillator is a differential oscillator.

3. The wireless intraocular pressure monitoring device as claimed in claim 1, wherein said converting unit includes:
    a frequency converter coupled to said oscillator and operable to reduce the frequency of the at least one of the first and second oscillation signals so as to generate a reduced-frequency signal;
    a frequency-to-voltage converter coupled to said frequency converter and operable to perform frequency-to-voltage conversion upon the reduced-frequency signal so as to obtain a converted voltage; and
    an output converter coupled to said frequency-to-voltage converter and operable to convert the converted voltage into the output signal.

4. A detecting module adapted for detecting a metal layer that deforms according to intraocular pressure, said detecting module comprising:
    first and second waveguides;
    an oscillator coupled to said first and second waveguides and operable to generate first and second oscillation signals that are substantially 180° out-of-phase, that are fed to said first and second waveguides respectively, and that have a frequency dependent on an equivalent impedance of said first and second waveguides, one of said first and second waveguides wirelessly transmitting an electromagnetic wave for reflection by the metal layer, the other one of said first and second waveguides wirelessly receiving the electromagnetic wave reflected by the metal layer, the equivalent impedance of said first and second waveguides varying according to the electromagnetic wave reflected by and received from the metal layer such that the equivalent impedance of said first and second waveguides further corresponds to the intraocular pressure; and
    a converting unit coupled to said oscillator and operable for receiving at least one of the first and second oscillation signals and for converting the frequency of the at least one of the first and second oscillation signals into an output signal corresponding to the intraocular pressure.

5. The detecting module as claimed in claim 4, wherein said oscillator is a differential oscillator.

6. The detecting module as claimed in claim 4, wherein said converting unit includes:
    a frequency converter coupled to said oscillator and operable to reduce the frequency of the at least one of the first and second oscillation signals so as to generate a reduced-frequency signal;
    a frequency-to-voltage converter coupled to said frequency converter and operable to perform frequency-to-voltage conversion upon the reduced-frequency signal so as to obtain a converted voltage; and
    an output converter coupled to said frequency-to-voltage converter and operable to convert the converted voltage into the output signal.

* * * * *